United States Patent [19]

Beaulieu et al.

[11] Patent Number: 5,484,771
[45] Date of Patent: Jan. 16, 1996

[54] ANTIHERPES PEPTIDE DERIVATIVES HAVING A 1,4-DIOXO-C, N-TERMINUS

[75] Inventors: Pierre L. Beaulieu, Montréal; Robert Déziel, Ville Mont-Royal; Neil Moss, Laval, all of Canada

[73] Assignee: Bio-Mega/Boehringer Ingelheim Research Inc., Quebec, Canada

[21] Appl. No.: 219,600

[22] Filed: Mar. 29, 1994

Related U.S. Application Data

[63] Continuation of Ser. No. 994,214, Dec. 18, 1992, abandoned, which is a continuation of Ser. No. 711,232, Jun. 6, 1991, abandoned.

[51] Int. Cl.$^6$ ................................................. A61K 38/06
[52] U.S. Cl. ........................... 514/18; 514/17; 514/19; 530/331; 562/561; 562/571
[58] Field of Search ............... 514/17, 18; 530/331; 562/561, 571

[56] References Cited

PUBLICATIONS

Gaudreau J Biol Chem 262, 12413, 1987.

*Primary Examiner*—Jill Warden
*Assistant Examiner*—David Lukton
*Attorney, Agent, or Firm*—R. P. Raymond; M-E. M. Devlin; A. R. Stempel

[57] ABSTRACT

Described herein are peptide derivatives of the formula $R^1NH$—CO—Q—C(O)—$NR^2$—CH[$CH_2$C(O)—Y]—C(O)—NH—CH[$CR^3(R^4)$—COOH]—C(W)—NH—$CHR^5$—Z wherein $R^1$ is an optionally substituted alkyl or optionally substituted phenylalkyl, $R^2$ is hydrogen or alkyl, $R^3$ and $R^4$ each independently is hydrogen or alkyl, or $R^3$ and $R^4$ are joined to form a cycloalkyl. $R^5$ is alkyl, cycloalkyl or (cycloalkyl)alkyl, Q is a divalent radical, for example, —$CH_2CH_2$—, —CH=CH— or 1,2-cyclohexanediyl, which serves as a two carbon spacer. W is oxo or thioxo, Y is, for example, an alkoxy or a monosubstituted or disubsdtuted ammo, and Z is a terminal unit, for example, hydrogen, COOH or $CH_2OH$. The derivatives are useful for treating herpes infections.

8 Claims, No Drawings

ANTIHERPES PEPTIDE DERIVATIVES HAVING A 1,4-DIOXO-C, N-TERMINUS

This is a continuation of application Ser. No. 07/994,214 filed Dec. 18, 1992, now abandoned, which is a continuation of application Ser. No. 07/711,232, filed Jun. 6, 1991, now abandoned.

FIELD OF THE INVENTION

This invention relates to peptide derivatives having antiviral properties and to means for using the derivatives to treat vital infections. More specifically, the invention relates to peptide derivatives (hereinafter called "peptides") exhibiting activity against herpes viruses, to pharmaceutical compositions comprising the peptides, and to a method of using the peptides to treat herpes infections.

BACKGROUND OF THE INVENTION

The family of herpes viruses is responsible for a wide range of infections that afflict humans and many important domestic animals. The diseases caused by these viruses range from bothersome cold sores to highly destructive infections of the central nervous system (encephalitis). The more common members of this family include herpes simplex virus (types 1 and 2) responsible for cold sores and genital lesions; varicella zoster virus which causes chicken pox and shingles; and Epstein-Bart virus which causes infectious mononucleosis. Although some significant advances have been made in the last decade in antiviral therapy, the need for effective, safe therapeutic agents for treating herpes vital infections continues to exist. For a recent review of current therapeutic agents in this area, see M. C. Nahata, "Antiviral Drugs: Pharmacokinetics, Adverse Effects and Therapeutic Use", J. Pharm. Technol., 3, 100 (1987).

The present application discloses a group of peptide derivatives having activity against herpes viruses. The relatively selective action of these peptides against herpes viruses, combined with a wide margin of safety, renders the peptides as desirable agents for combating herpes infections.

The association of peptides with anti-herpes activity is uncommon. Instances of reports of such an association include B. M. Dutia et al., Nature, 321, 439 (1986), E. A. Cohen et al., Nature, 321, 441 (1986), J. H. Subak-Sharpe et at., UK patent application 2185024, published Jul. 8, 1987, E. A. Cohen et al., European patent application Ser. No. 246630, published Nov. 25, 1987, R. Freidinger et al., European patent application 292255, published Nov. 23, 1988, R. Freidinger et al., U.S. Pat. No. 4,814,432, issued Mar. 21, 1989, V. M. Garsky et al., U.S. Pat. No. 4,837,304 issued Jun. 6, 1989, and R. Colonno et al., U.S. Pat. No. 4,845,195, issued Jul. 4, 1989. The subject peptides of the previous reports can be distinguished from the peptides of the present application by characteristic structural and biological differences.

SUMMARY OF THE INVENTION

The peptides of this invention are represented by formula 1

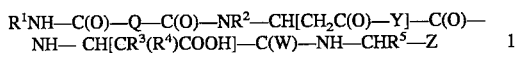

wherein $R^1$ is (1–10C)alkyl, (1–10C)alkyl mononsubstituted with halo, hydroxy or lower alkoxy, lower cycloalkyl, (lower cycloalkyl)-(lower alkyl), phenyl(lower)alkyl or phenyl(lower)alkyl monosubstituted with halo, hydroxy or lower alkoxy;

$R^2$ is hydrogen or lower alkyl;

$R^3$ and $R^4$ each independently is hydrogen or lower alkyl or $R^3$ and $R^4$ together with the carbon atom to which they are attached form a lower cycloalkyl;

$R^5$ is lower alkyl, lower cycloalkyl or (lower cycloalkyl)-(lower alkyl);

Q is a divalent radical selected form the group consisting of:

(a) —$CHR^6CR^7R^8$— wherein $R^6$, $R^7$ and $R^8$ each independently is hydrogen or lower alkyl, or $R^6$ and $R^7$ together with the carbon atoms to which they am attached form a lower cycloalkyl and $R^8$ is hydrogen, (b) —CH=CH—, or (c)

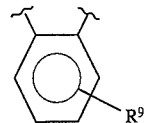

wherein $R^9$ is hydrogen, halo, hydroxy, lower alkoxy, amino, lower alkylamino or di(lower alkyl)amino;

W is oxo or thioxo;

Y is (a) (1–14C)alkoxy, (3–14)alkenyloxy, $CH_3(OCH_2CH_2)_n$—O wherein n is the integer 1, 2 or 3, lower cycloalkyloxy, lower alkoxy monosubstituted with a lower cycloalkyl, phenoxy, phenoxy monosubstituted with hydroxy, halo, lower alkyl or lower alkoxy, phenyl(lower)alkoxy or phenyl(lower)alkoxy in which the aromatic portion thereof is substituted with hydroxy, halo, lower alkyl or lower alkoxy, or (b) $NR^{10}R^{11}$ wherein $R^{10}$ is lower alkyl and $R^{11}$ is lower alkoxy, or (c) $NR^{10}R^{11}$ wherein $R^{10}$ is hydrogen or lower alkyl and $R^{11}$ is (1– 14C)alkyl, lower cycloalkyl, lower alkyl monosubstituted with a lower cycloalkyl; phenyl, phenyl monosubstituted with halo, lower alkyl or lower alkoxy; phenyl(lower)alkyl, phenyl(lower)alkyl in which the aromatic portion thereof is substituted with halo, lower alkyl or lower alkoxy; or (Het)-lower alkyl wherein Her represents a five or six membered heterocyclic radical containing one or two heteroatoms selected from nitrogen, oxygen or sulfur, or (d) $NR^{10}R^{11}$ wherein $R^{10}$ and $R^{11}$ together with the nitrogen to which they are attached form an azetidino, pyrrolidino, piperidino, morpholino, thiomorpholino, piperazino, 4-(lower alkyl)piperazino or 3,3,5-trimethylhexahydroazepino; or (e) (1–14C)alkyl, lower cycloalkyl, lower alkyl monosubstituted with a lower cycloalkyl, phenyl(lower)alkyl, phenyl(lower)alkyl wherein the aromatic portion thereof is substituted with halo, lower alkyl or lower alkoxy, or (Het)-lower alkyl wherein Het represents a five or six membered heterocyclic radical containing one or two heteroatoms selected from nitrogen, oxygen or sulfur, and Z is hydrogen, COOH, $CH_2COOH$, $CH_2OH$ or 5-1H-tetrazolyl; or a therapeutically acceptable salt thereof A preferred group of peptides of this invention is represented by formula 1 wherein $R^1$, $R^2$, $R^3$, $R^4$, $R^5$ and W are as defined hereinabove; Q is divalent radical selected from the group consisting of:

(a) —CHR⁶CR⁷R⁸— wherein R⁶ is hydrogen and R⁷ and R⁸ each independently is hydrogen or lower alkyl, or R⁶ and R⁷ together with the carbon atoms to which they are attached form a cyclohexyl and R⁸ is hydrogen, (b) —CH=CH— in the cis conformation, or (c)

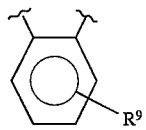

wherein R⁹ is hydrogen, chloro, fluoro, hydroxy or methoxy;

Y is (a) ( 1–14C)alkoxy, lower cycloalkyloxy, lower cycloalkylmethoxy, phenyl(lower)alkoxy; or (b) NR¹⁰R¹¹ wherein R¹⁰R¹¹ wherein R¹⁰ is lower alkyl and R¹¹ is lower alkoxy; or (c) NR¹⁰R¹¹ wherein R¹⁰ is hydrogen or lower alkyl and R¹¹ is (1–14C)alkyl, (3–14C)alkenyloxy, CH₃(OCH₂CH₂)₃—O, lower cycloalkyl, lower cycloalkylmethyl, phenyl, phenyl monosubstituted with halo, lower alkyl or lower alkoxy, phenyl(lower)alkyl, phenyl(lower)alkyl monosubstituted with halo, lower alkyl or lower alkoxy, (Het)-lower alkyl wherein Het is a heterocyclic radical selected from 2-pyrrolyl, 2-pyridinyl, 4-pyridinyl, 2-furyl, 2-isoxazolyl and 2-thiazolyl; or (d) NR¹⁰R¹¹ wherein R¹⁰ and R¹¹ together with the nitrogen atom to which they are attached form an azetidino, pyrrolidino, piperidino, morpholino or 3,3,5-trimethylhexahydroazepino; or (e) ( 1–14C)alkyl, lower cycloalkyl, lower cycloalkylmethyl, phenyl(lower)alkyl or (Het)-lower alkyl wherein Het is a heterocyclic radical selected from 2-pyrrolyl, 2-piperidinyl, 4-piperidinyl, 2-furyl, 2-isoxazolyl or 2-thiazolyl; and Z is hydrogen, COOH, CH₂COOH or CH₂OH; or a therapeutically acceptable salt thereof.

A more preferred group of the peptides is represented by formula 1 wherein R¹ is (1–10C)alkyl, ( 1–10C)alkyl monosubstituted with hydroxy, lower cycloalkyl or (lower cycloalkyl)methyl; R² is hydrogen or methyl; R³ and R⁴ each independently is hydrogen, methyl, ethyl or propyl, or R³ and R⁴ together with the carbon atom to which they are attached form a lower cycloalkyl; R⁵ is 1-methylethyl, 1,1-dimethylethyl, 1-methylpropyl, 2-methylpropyl, 2,2-dimethylpropyl, cyclopentyl, cyclopentylmethyl, cyclohexyl or cyclohexylmethyl; Q is 1,2-ethanediyl (also known as ethylene), 2,2-dimethyl- 1,2-ethanediyl, 2(S)-(1,1-dimethylethyl)-1,2-ethanediyl, 2(S)-( 1-methylethyl)-1,2-ethanediyl, cis-1,2-cyclohexanediyl, cis-1,2-ethenediyl or 1,2-phenylene; W is oxo; and Y is (1–14C)alkoxy, (3–14C)alkenyloxy, CH₃(OCH₂CH₂)₃—O, lower cycloalkyloxy, lower cycloalkylmethoxy, phenyl(lower)alkoxy; NR¹⁰R¹¹ wherein R¹⁰ is lower alkyl and R¹¹ is lower alkoxy, or NR¹⁰ R¹¹ wherein R¹⁰ is hydrogen or lower alkyl and R¹¹ is (1–14C)alkyl, lower cycloalcyl, lower cycloalkylmethyl, phenyl, phenyl(lower)alkyl or pyridinyl(lower alkyl), or NR¹⁰R¹¹ wherein R¹⁰ and R¹¹ together with the nitrogen to which they are attached form an azetidino, pyrrolidino, piperidino, morpholino or 3,3,5-trimethylhexahydroazepino; or ( 1–14C)alkyl, lower cycloalkyl, lower cycloalkylmethyl, phenyl(lower alkyl) or pyridinyl(lower alkyl); and Z is hydrogen, COOH, CH₂COOH or CH₂OH; or a therapeutically acceptable salt thereof.

A most prefered group of the peptides is represented by formula 1 wherein R¹ is 1-ethylpropyl, 1-methylethyl or cyclohexyl; R², R³ and R⁴ are as defined in the last instance; R⁵ is 2-methylpropyl or 2,2-dimethylpropyl; Q is 1,2-ethanediyl, 2,2-dimethyl- 1,2-ethanediyl, 2(S)-(1,1-dimethylethyl)-1,2-ethanediyl, 2(S)-(1-methylethyl)- 1,2-ethanediyl, cis-1,2-cyclohexanediyl, cis-1,2-ethenediyl or 1,2-phenylene; W is oxo; Y is hexyloxy, 1-methylheptyloxy, octyloxy, decyloxy, CH₃(OCH₂CH₂)₃–O, phenylpropoxy, N(Me)OMe, ethylamino, phenylamino, phenylethylamino, N-methyl-N-phenylethylamino, N,N-dimethylamino, N,N-diethylamino, N,N-diisopropylamino, N-methyl-N-octylamino, azetidino, pyrrolidino, piperidino, morpholino, 3,3,5-trimethylhexahydroazepino, methyl, hexyl, heptyl, 1-methylheptyl, decyl, undecyl, cyclopentyl, cyclohexyl, cyclohexylmethyl or phenylpropyl; and Z is hydrogen, COOH or CH₂OH; with the proviso that when Z is hydrogen then R³ is hydrogen, methyl or ethyl and R⁴ is methyl or ethyl, or R³ and R⁴ together with the carbon atom to which they are attached form a lower cycloalkyl; or a therapeutically acceptable salt thereof.

Included within the scope of this invention is a pharmaceutical composition comprising an anti-herpes vitally effective amount of a peptide of formula 1, or a therapeutically acceptable salt thereof, and a pharmaceutically or veterinarily acceptable carrier.

Also included within the scope of this invention is a cosmetic composition comprising a peptide of formula 1, or a therapeutically acceptable salt thereof, and a physiologically acceptable carrier suitable for topical application.

An important aspect of the invention involves a method of treating a herpes viral infection in a mammal by administering to the mammal an anti-herpes virally effective mount of the peptide of formula 1, of a therapeutically acceptable salt thereof.

Another important aspect involves a method of inhibiting the replication of herpes virus by contacting the virus with a herpes vital ribonucleotide reductase inhibiting amount of the peptide of formula 1, or a therapeutically acceptable salt thereof.

Processes for preparing the peptides of formula 1 are described hereinafter.

Details of the Invention

GENERAL

Alternatively, formula 1 can be illustrated as:

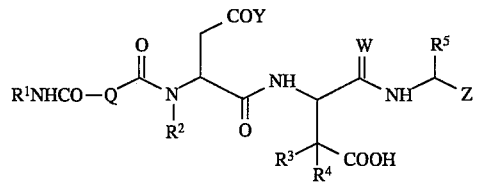

The term 'residue' with reference to an amino acid or amino acid derivative means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commision of Biochemical Nomenclature, see European Journal of Biochemistry 138, 9 (1984). For instance, Gly, Val, Thr, Ala, He, Asp, Ser and Leu represent the residues of glycine, L-valirte, L-threonine, L-alanine, L-isoleucine, L-aspartic acid, L-serine and L-leucine, respectively.

The asymmetric carbon atoms residing in the principal linear axis (i.e. the backbone) of the peptides of formula 1, exclusive of the terminal groups, have an S configuration. Asymmetric carbon atoms residing in the side chain of an amino acid or derived amino acid residue, including those in terminal groups, may have the S or R configuration.

The symbol "Tbg" represents the amino acid residue of 2(S)-amino- 3,3-dimethylbutanoic acid. The symbol "Cpg" represents the amino acid residue of (S)-α-aminocyclopentaneacetic acid. The symbol "γMeLeu" represents the amino acid residue of 2(S)-amino- 4,4-imethylpentanoic acid. The symbol "L-γMe-leucinol" represents 2(S)-amino-4,4-dimethylpentanol with one hydrogen removed from the α-amino group.

Other symbols used herein are: (N—Me)Asp for the residue of (S)-2-(methylamino)butanedioic acid; Asp(cyBu) for the residue of (S)-α-amino-1-carboxycyclobutaneacetic acid; Asp(cyPn) for the residue of (S)-α-amino-1-carboxycyclopentaneacetic acid; Asp(pyrrolidino) for the residue of the amide 2(S)-amino-4-oxo-4-pyrrolidinobutanoic acid; and Asp(morpholino), Asp(NEt$_2$) and Asp(N—Me—N-octyl) similarly represent the residues of the corresponding amides wherein the pyrrolidino is replaced with morpholino, diethylamino and N-methyl-N-octylamino, respectively. The symbols "Asp(diMe)" represents the residue of 2(S)-amino-3,3-dimethylbutanedioic acid, i.e. 3,3-dimethyl-L-aspartic acid. Similarly, Asp(diEt), Asp(Bu) and Asp(Me) represent the residues of 3,3-diethyl-L-aspartic acid, 3-butyl-L-aspartic acid and 3-methyl-L-aspartic acid, respectively.

The term 'halo' as used herein means a halo radical selected from bromo, chloro, fluoro or iodo.

The term "lower alkyl" as used herein, either alone or in combination with a radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl.

The term "lower cycloalkyl" as used herein, either alone or in combination with a radical, means saturated cyclic hydrocarbon radicals containing from three to six carbon atoms and includes cyclopropyl, cyclobutyl, cyclopentyl and cyclohexyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as temarybutyloxy.

The term "amino" as used herein means an amino radical of formula —NH$_2$. The term "lower alkylamino" as used herein means alkylamino radicals containing one to six carbon atoms and includes methylamino, ethylamino, propylamino, 1-methyl-ethyl-amino and 2-methylbutylamino. The term "di(lower alkyl)amino" means an amino radical having two lower alkyl substitutents each of which contains one to six carbon atoms and includes dimethylamino, diethylamino, ethylmethylamino and the like.

The term "(1–10C)alkyl" as used herein means straight and branched chain alkyl radicals containing from one to ten carbon atoms. The term "(1–14.C)alkyl" as used herein means straight and branched chain alkyl radicals containing from one to fourteen carbon atoms.

The term "phenyl(2–10C)alkanoyl" as used herein means phenyl substituted 1-oxoalkyl radicals wherein the 1-oxoalkyl portion thereof is a straight or branched chain 1-oxoalkyl containing from two to ten carbon atoms; for example, 1-oxo-3-phenylpropyl and 1-oxo- 5-methyl-6-phenylhexyl. The term "phenyl(3–10C)alkenoyl" as used herein means phenyl substituted 1-oxoalkenyl radicals wherein the 1-oxoalkenyl portion thereof is a straight or branched chain 1-oxalkenyl containiing from three to ten carbon atoms; for example, 2-methyl- 1-oxo-3-phenyl-3-pentenyl.

The symbol "Ψ[CSNH]" used between the three letter representations of two amino acid residues means that the normal amide bond between those residues in the peptide, being represented, has been replaced with a thioamide bond.

The term "pharmaceutically acceptable carrier" or "veterinarily acceptable carrier" as use herein means a non-toxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "effective amount" means a predetermined antiviral amount of the antiviral agent, i.e. an amount of the agent sufficient to be effective against the vital organisms in vivo.

The term "coupling agent" as used herein means an agent capable of effecting the dehydrative coupling of an amino acid or peptide free carboxy group with a free amino group of another amino acid or peptide to form an amide bond between the reactants. Similarly, such agents can effect the coupling of an acid and an alcohol to form corresponding esters. The agents promote or facilitate the dehydrative coupling by activating the carboxy group. Descriptions of such coupling agents and activated groups are included in general text books of peptide chemistry; for instance, E. Schröder and K. L. Lübke, "The Peptides", Vol. 1, Academic Press, New York, N.Y., 1965, pp 2–128, and K. D. Kopple, "Peptides and Amino acids", W. A. Benjamin, Inc., New York, N.Y., 1966, pp 33– 51. Examples of coupling agents are thionyl chloride, diphenylphosphoryl azide, 1,1'-carbonyldiimidazole, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris(dimethylamino)-phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole.

Process

The peptides of formula 1 can be prepared by processes which incorporate therein methods commonly used in peptide synthesis such as classical solution coupling of amino acid residues and/or peptide fragments, and if desired solid phase techniques. Such methods are described, for example, by E. Schröder and K. Lübke, cited above, in the textbook series, "The Peptides: Analysis, Synthesis, Biology", E. Gross et at., Eds., Academic Press, New York, N.Y., 1979–1987, Volumes 1 to 8, and by J. M. Stewart and J. D.

Young in "Solid Phase Pepride Synthesis", 2nd ed., Pierce Chem. Co., Rockford, Ill., USA, 1984.

A common feature of the aforementioned processes for the peptides is the protection of the reactive side chain groups of the various amino acid residues or derived am/no acid residues with suitable protective groups which will prevent a chemical reaction from occurring at that site until the protective group is ultimately removed. Also common is the protection of an α-amino group on an amino acid or a fragment while that entity reacts at the carboxy group, followed by the selective removal of the α-amino protective group to allow subsequent reaction to take place at that location. Another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

In general, therefore, a peptide of formula 1 can be prepared by the stepwise coupling in the order of the sequence of the peptide of the amino acid or derived amino acid residues, or fragments of the peptide, which if required are suitably protected, and eliminating all protecting groups, if present, at the completion of the stepwise coupling to obtain the peptide of formula 1. More specific processes are illustrated in the examples hereinafter.

The peptide of formula 1 of this invention can be obtained in the form of a therapeutically acceptable salt. In the instance where a particular peptide has a residue which functions as a base, examples of such salts of the base are those with organic acids, e.g. acetic, lactic, succinic, benzoic, salicylic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phorphoric acid. If desired, a particular acid addition salt is converted into another acid addition salt, such as a non-toxic, pharmaceutically acceptable salt, by treatment with the appropriate ion exchange resin in the manner described by R. A. Boissonnas et at., Helv. Chim. Acta, 43, 1849 (1960).

In the instance where a particular peptide has one or more free carboxy groups, examples of such salts of the caxboxy group are those with the sodium, potassium or calcium cations, or with strong organic bases, for example, triethylamine or N-methylmorpholine.

Antiherpes Activity

The antiviral activity of the peptides of formula 1 can be demonstrated by biochemical, microbiological and biological procedures showing the inhibitory effect of the compounds on the replication of herpes simplex viruses, types 1 and 2 (HSV-1 and HSV-2), and other herpes viruses, for example, varicella zoster virus (VZV), Epstein-Bart virus (EBV), equine herpes virus (EHV) and cytomegalovirus.

Noteworthy is the fact that all of the aforementioned viruses are dependent on their own ribonucleotide reductase to synthesize deoxyribonucleotides for their replication. Although this fact may not be directly linked with the antiviral activity found for the present peptides, the latter compounds have been shown so far to have antiviral properties against all viruses dependent on ribonucleotide reductase to synthesize DNA for their replication.

In the examples hereinafter, the inhibitory effect on herpes ribonucleotide reductase is noted for exemplary peptides of formula 1. Noteworthy, in the connection with this specific inhibition of herpes ribonucleotide reductase, is the relatively minimal effect or absence of such an effect of the peptides on cellular ribonucleotide reductase activity required for normal cell replication.

A method for demonstrating the inhibitory effect of the peptides of formula 1 on viral replication is the cell culture technique; see, for example, T. Spector et al., Proc. Natl. Acad. Sci. USA, 82, 4254 (1985).

The therapeutic effect of the peptides can be demonstrated in laboratory animals, for example, by using an assay based on genital herpes infection in Swiss Webster mice, described by E. R. Kern, et al., Antiviral Research, 3, 253 (1983).

When a peptide of this invention, or one of its therapeutically acceptable salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the peptide, chosen route of administration and standard biological practice. For topical administration, the peptide can be formulated in pharmaceutically accepted vehicles containing 0.1 to 10 percent, preferably 0.5 to 5 percent, of the active agent. Such formulations can be in the form of a solution, cream or lotion.

For systemic administration, the peptide of formula 1 is administered by either intravenous, subcutaneous or intramuscular injection, in compositions with pharmaceutically acceptable vehicles or careers. For administration by injection, it is preferred to use the peptide in solution in a sterile aqueous vehicle which may also contain other solutes such as buffers or preservatives as well as sufficient quantifies of pharmaceutically acceptable salts or of glucose to make the solution isotonic.

Suitable vehicles or careers for the above noted formulations are described in standard pharmceutical texts, e.g. in "Remingtons Pharmaceutical Sciences", 17th ed, Mack Publishing Company, Easton, Pa., 1985.

The dosage of the peptide will vary with the form of administration and the particular active agent chosen. Furthermore, it will vary with the particular host under treatment. Generally, treatment is initiated with small increments until the optimum effect under the circumstances is reached. In general, the peptide is most desirably administered at a concentration level that will generally afford antivirally effective results without causing any harmful or deleterious side effects.

With reference to topical application, the peptide is administered cutaneously in a suitable topical formulation to the infected area of the body e.g. the skin or pan of the oral or genital cavity, in an amount sufficient to cover the infected area. The treatment should be repeated, for example, every four to six hours until lesions heal.

With reference to systemic administration, the peptide of formula 1 is administered at a dosage of 10 mcg to 1000 mcg per kilogram of body weight per day, although the aforementioned variations will occur. However, a dosage level that is in the range of from about 50 mcg to 500 mcg per kilogram of body weight per day is most desirably employed in order to achieve effective results.

Another aspect of this invention comprises a cosmetic composition comprising a herpes vital prophylactic amount of the peptide of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the peptide than corresponding pharmaceutical compositions for topical application. A preferred range of the amount of the peptide in the cosmetic composition is 0.01 to 0.2 percent by weight.

Although the formulation disclosed hereinabove are indicated to be effective and relatively safe medications for treating herpes viral infections, the possible concurrent administration of these formulations with other antiviral medications or agents to obtain beneficial results is not excluded. Such other antiviral medications or agents include acyclovir and antiviral surface active agents or antiviral intefferons such as those disclosed by S. S. Asculai and F. Rapp in U.S. Pat. No. 4,507,281, Mar. 26, 1985.

The following examples illustrate further this invention. Solution percentages express weight to volume relationship, unless stated otherwise. Abbreviations used in the examples include BOP: (benzotriazol-1-yloxy)tris(dimethylamino)-phosphonium hexafluoro phosphate; Bzl: benzyl; $CH_2Cl_2$: methylenedichloride; DMF: dimethylformamide; DIPEA: diisopropylethylamine; $Et_2O$: diethyl ether;, EtOAc: ethyl acetate; EtOH: ethanol; HPLC: high performance liquid chromatography; NMM: N-methylmorpholine; TFA: trifluoroacetic acid; TLC: thin layer chromatography. Temperatures are given in degrees centigrade.

EXAMPLE 1

Preparation of the Intermediate
4-Cyclohexylamino-4-oxobutanoic Acid

Succinic anhydride (2.59 g, 25.9 retool) was dissolved in pyridine (15 ml). Cyclohexylamine was added dropwise to the solution at 0°. Thereafter, the mixture was stirred at room temperature (20°–22°) for 6 h. The pyridine was removed under reduced pressure. The residue was poured into 10% aqueous citric acid. The resulting precipitate was collected, washed thoroughly with 10% aqueous citric acid and then water. The precipitate was dried under vacuum to give the title compound (3.81 g, 74%), mp 168°–170°. The structure of the product was confirmed by NMR.

Replacement of succinic anhydride with the appropriate anhydride derived from the acid of formula HOOC—Q—COOH wherein Q is as defined herein and/or replacement of cyclohexylamine with the appropriate amine of formula $R^1NH_2$ wherein $R^1$ is as defined herein affords the corresponding intermediate of formula $R^1NHCO$—Q—COOH. For instance, replacement of succinic anhydride with cis-1,2-cyclohexane dicarboxylic acid and replacement of cyclohexylamine with 1-ethylpropylamine gave d,l-cis-2-[(1-ethylpropylamino)-carbonyl] cyclohexanecarboxylic acid.

EXAMPLE 2

Preparation of the Intermediate
Boc—Asp(pyrrolidino)—OH

N,N'-Carbonyldiimidazole (24.32 g, 0.15 mol) was added in small portions to a stirred solution of Boc—Asp-OBzl (47.60 g, 0.147 mol) in acetonitrile (500 ml). After 45 rain, the reaction mixture was cooled to 0° and pyrrolidine (13.4 ml, 0.16 mol) was added dropwise. Thereafter, the mixture was stirred at room temperature to complete the reaction (about 3 h as judged by TLC). The solvent was removed under reduced pressure and the residue was dissolved in EtOAc (500 ml). The organic phase was washed with 10% aqueous HCl (3×100 ml), 1N aqueous NaOH (2×100 ml) and dried ($MgSO_4$). Evaporation of the organic phase under reduced pressure gave a colorless oil which solidified on standing. The latter product in a solution of EtOH (200 ml) was subjected to hydrogenolysis for 20 h at atmospheric pressure using 200 mg of 20% by weight of $Pd(OH)_2$ on carbon as the catalyst. The reaction mixture was filtered through diatomaceous earth. Evaporation of the filtrate afforded a residue which was purified by recrystallization from hexane/$Et_2O$ to give the desired product (37.10 g, 88%), mp 114°–116°. The structure of the product was confirmed by NMR.

Corresponding N-substituted asparagine analogs can be obtained by replacing pyrrolidine in the procedure of this example with the appropriate amine (e.g. diethylamine or N,O-dimethylhydroxylamine).

EXAMPLE 3

Preparation of the Intermediate Boc—Asp[1
(S)-methylheptyloxy]—OH

A solution of Boc—Asp-OBzl (10.2 g, 31.6 mmol) in acetonitrile was added at 0° to a mixture of N,N'-carbonyl diimidazole (5.6 g, 34.7 mmol), DIPEA (8 ml, 46 mmol), 2(S)-octanol (6 ml, 37.9 mmol) and 4-dimethylaminopyridine (200 mg). The mixture was stirred for 3 h and then concentrated to dryness. The residue was dissolved in EtOAc. The solution was washed with 1N aqueous HCl, 1N aqueous $NaHCO_3$, dried ($MgSO$,) and concentrated. The resultant oil was purified by chromatography [$SiO_2$, eluent: hexane-EtOAc (7:3)] to give Boc—Asp[1(S)-methylheptyloxy]-OBzl (92% yield). Hydrogenation of the latter compound in the presence of 20% $Pd(OH)_2/C$ in ethanol solution afforded a quantitative yield of the title compound as a solid. NMR(200 MHz, $CDCl_3$)δ 0.9(m,3H), 1.25(m, 10H), 1.45(s, 9H), 2.8(dd, 1H), 3.0(rid, Ill), 4.6(m, 1H), 4.95 (m, 1H) and 5.55(d, 1H).

Analogous esters of Boo—Asp—OH were prepared in the same manner.

EXAMPLE 4

Preparation of the Intermediate
Boc-2(S)-Amino-5-cyclopentyl-4-oxopentanoic
Acid Boc-2(S)-amino-4-keto-1,6-hexanedioic acid 1-benzyl ester 6-(4-nitrophenyl)methyl ester (4.8 g, 9.6 mmol) was dissolved in DMF (100 ml). $Na_2CO_3$ (4.07 g, 38.4 mmol) and 1,4-diiodobutane (3.59 g, 11.6 mmol) were added to the solution. The mixture was stirred 18 h at room temperature and then heated at 50 ° for 3 h. Evaporation of the solvent, dissolution of the resulting residue with EtOAc, washing of the resulting solution with 1N aqueous HCl and water, followed by drying ($MgSO_4$) and evaporation gave a crude product. The crude product was purified by chromatography eluent: hexane-EtOAc (4:1)] to give the corresponding benzyl ester of the title compound (4.3 g). The benzyl ester was subjected to hydrogenolysis [20% $Pd(OH_2)/C$ in MeOH, 18 h] and worked up (see example 1) to give the title compound (140 mg). NMR and MS of the product were in agreement with the expected structure.

Analogous derived amino acid intermediates having a ketone in their side chain were prepared in a similar manner as described for this example using the appropriate alkyl iodide.

EXAMPLE 5

Preparation of the Intermediate
Boc—Asp(OBzl)Ψ[CSNH]Leu-OBzl

A stirred mixture of Boc—Asp(OBzl)Leu-OBzl (2.90g, 5.51 mmol) and Lawesson's reagent (1.12 g, 2.7 mmol), see "U. Pederson et al., Tetrahedron, 38, 3267 (1982), in toluene (30ml) was heated at reflux for 2 h. Column chromatography ($SiO_2$, eluent: $CH_2Cl_2$) gave the title compound as a yellow oil (major fraction of 2 g), MS: 543 $(M+H)^+$.

Analogous thioamides were prepared in the same manner.

EXAMPLE 6

Preparation of 3-Alkyl- or 3,3-Dialkyl-L-aspartic
Acid Intermediates and
2(S)-Amino-3-(1-carboxycycloalkyl)acetic Acid
Intermediates These intermediates, which can be used to prepare compounds of formula 1 in which $R^3$ and $R^4$ are other then hydrogen, can be prepared according to the method of M. Bochenska and J. F. Biernat, Rocz. Chem., 50, 1195 (1976); see Chem. Abstr., 86, 43990r (1977).

For example, (±)-Boc—Asp(cyPn)(OBzl)—OH was prepared as follows: To a solution of 1-bromocyclopentanecarboxylic acid ethyl ester [17.1g, 77.3 mmol, described by D. N. Harpp et at., J. Org. Chem., 46, 3420 (1975)]and freshly distilled ethyl isocyanoacetate (12.7 g, 122 mmol) in a mixture of dimethylsulfoxide and $Et_2O$ (1:1, 120 ml) was added sodium hydride (4.5 g, 60% dispersion in mineral off, 122 mmol) in small portions over 5 h. The resulting red slurry was stirred at room temperature for 16 h after which time it was treated with a saturated aqueous solution of ammonium chloride (5 ml). The resulting mixture was diluted with water (500 ml) and extracted (2×) with EtOAc. The EtOAc layers were combined and washed with water (2×) and then with brine. Drying ($MgSO_4$), filtering and concentration of the extract afforded a dark red off. This material was subjected to flash chromatography through a 5× 25 cm column of silica gel [eluent: EtOAc-hexane (1:10)]. Concentration of the appropriate fractions provided α-cyano-1-carboxycyclopentaneacetic acid diethyl ester as a clear colorless viscous liquid (13 g, 66 %).

The latter compound (13 g, 51 mmol) was mixed with 6N aqueous HCl (60 ml) at 0°. After dissolution, the reaction mixture was heated in a oil bath at 120° for 24 h. After this time water was removed from the mixture using a dry ice rotary evaporator. The resulting white solid was dried under high vacuum for 18 h. The dried material was dissolved in a mixture of dioxane (50 ml) and 3N aqueous NaOH (52 ml). A solution of di(tertiarybutyl) dicarbonate (14.6 g, 67 mmol) in dioxane (25 ml) was added to the solution. The mixture was stirred at room temperature for 16 h. Additional 3N aqueous NaOH was added at intervals to keep the pH of the mixture at about 10. The mixture was diluted with water (500 ml) and extracted (2×) with $Et_2O$ (200 ml). The aqueous phase was rendered acidic (pH =3) with solid citric acid and extracted (2×) with EtOAc (300 ml). The combined EtOAc extracts were washed with water (3×) and brine. Drying, filtering and concentration of the extract afforded Boc—Asp(cyPn)—OH as a white solid (14 g, 96%).

To a solution of the latter compound (7.2 g, 25 mmol) in dry DMF (50 ml) was added $K_2CO_3$ (7.6 g, 55 mmol) and benzyl bromide (6.6 ml, 55 mmol). The reaction mixture was stirred at room temperature for about 7 h. Thereafter, the reaction mixture was poured into a mixture of water (500 ml) and EtOAc (350 ml). The organic phase was washed with water (2×) and brine. Drying, filtering and concentration of the extract provided a pale yellow viscous liquid. This material was subjected to flash chromatography [$SiO_2$, eluent: hexane-EtOAc ( 12:1 )]. Concentration of the appropriate fractions provided the dibenzyl derivative of Boc—Asp-(cyPn)—OH as a low melting white solid (11 g, 94%). The dibenzyl product was dissolved in tetrahydrofuran (100 ml) and an aqueous solution of LiOH (23.5 ml, 1N) was added. After 4 h, the reaction mixture was poured into water and extracted (3×) with $Et_2O$. The aqueous phase was rendered acidic with 10% aqueous citric acid and extracted (2×) with EtOAc. The EtOAc layers were combined, dried ($MgSO_4$), filtered and concentrated to provide Boc—Asp-(cyPn)(OBzl)OH as a clear color less gum (7.3 g, 82%).

EXAMPLE 7

Preparation of
(S)-α-Azido-1-[(phenylmethoxy)carbonyl]
cyclopentaneacetic Acid Benzyl Ester The title compound was prepared from 2-oxaspiro[4.4] nonane- 1,3-dione, described by M. N. Aboul-Enein et at., Pharm. Acta Helv., 55, 50 (1980), according to the asymmetric azidation method utilizing the Evan's auxiliary, see D. A. Evans et al., J. Amer. Chem. Soc., 112, 4011 (1990). The NMR (200 MHz, $CDCl_3$) of the compound showed: δ 4.55 (s, 1H), 5.12 (s,2H) and 7.4 (m, 5H). The compound is used in example 11.

EXAMPLE 8

Preparation of (R,S)-3-(
1,1-dimethylethyl)-dihydro-2,5-furandione (a) A mixture of pivaldehyde (5.00 g, 58 mmol), ethyl-cyanoacetate (6.60g, 58.3 mmol), acetic acid (3.50 g, 58.3 mmol) and pyridine (4.60 g, 58.2 mmol) was heated at reflux for 1 h. A second portion of pivaldehyde (5.00 g, 58 mmol) was added. The refluxing of the mixture was continued for 18h. After cooling, the mixture was poured into 1N aqueous HCl (50 mL). The resulting mixture was extracted with EtOAc (3×50 mL). The combined organic layers, were washed with 1N aqueous HCl, dried ($MgSO_4$) and concentrated to give a colorless oil. The oil was purified by flash chromatography on $SiO_2$ using hexane-EtOAc (9:1) as the eluant to give 2-cyano- 4,4-dimethyl-2-pentenoic acid ethyl ester as a colorless oil (7.69 g, 73 % yield).

(b) The latter compound (7.69 g, 42.4 mmol) was mixed with glacial AcOH (2.60 g, 43 mmol) and anhydrous pyridine (3.42 g, 43 mmol). The mixture was heated to 5(P. Potassium cyanide was added, followed by the addition of anhydrous EtOH (6 mL). The mixture was heated at 50° for 45 min, cooled to room temperature and partitioned between 1N aqueous HCl (25 mL) and EhO (100 mL). The EhO layer was separated, washed with 1N aqueous HCl (2×20 mL) and brine (2×20 mL), dried (MgSO,) and concentrated to give 2,3-dicyano-4,4-dimethylpentanoic acid ethyl ester as a brown oil (8.83 g, 100% crude yield).

(c) The latter product (11 g) was suspended in concentrated HCl (150 mL). The mixture was heated at reflux for 24 h and then cooled in an ice bath. The resulting white solid precipitate was collected, washed with water and dried under vacuum. The solid was dissolved in EtOAc (300 mL). Insoluble material in the solution was removed by Filtration. The filtrate was concentrated under reduced pressure to give an oil. The oil was triturated with hexane. The resulting white crystalline material was collected to give (R,S)-2-(1, 1-dimethylethyl)- 1,4-butanedioic acid (7.95 g, 95% yield).

(d) The latter compound (7.95 g, 51 mmol) was suspended in acetic anhydride (11 mL, 117 mmol). The mixture was heated at 110° for 2 h. Subsequent distillation under vacuum of the mixture gave the title compound of this example as an off (bp 140°–145°/12 mm, 7.08 g, 88% yield). The oil solidified upon cooling.

EXAMPLE 9

Preparation of (R,S)-2-(1,1-Dimethylethyl)-4-oxo-4-(1-ethylpropylamino)butanoic Acid (R,S)-3-(1,1-dimethylethyl)-dihydro-2,5-furandione (5.00 g, 32 mmol, described in example 8) was dissolved in acetonitrile (50 mL). The solution was cooled to 0°. (1-Ethylpropyl)amine (6.13 g), 70.4 mmol) was added slowly to the stirred solution. The solution was stirred at room temperature for 18 h and then pardoned between $Et_2O$ and 10% aqueous citric acid (60 mL each). The organic phase was separated. The aqueous phase was extracted with $Et_2O$ (3×25 mL). The combined organic layers were washed with 10% aqueous citric acid (2×25 mL), brine (25 mL), dried ($MgSO_4$) and concentrated. The residue was triturated with $Et_2O$ to give the rifle compound as a white solid (4.65 g, 59% yield). The compound is used in example 11.

EXAMPLE 10

Preparation of
$Et_2$CHNHCOCH$_2$CH$_2$CO—Asp(pyrrolidiono)—Asp-Leu—OH

Boc—Asp(OBzl)—OH (162 mg, 0.5 mmol), TsOH.Leu-OBzl (1.57 mg, 0.4 mmol) and BOP (221 mg, 0.5 mmol) were dissolved in acetonitrile (10 ml). NMM (0.27 mi, 2.5 mmol) was added to the solution. The mixture was stirred at room temperature for 2 h, after which time the coupling was complete as judged by TLC. The solvent was removed by evaporation under reduced pressure. The residue was taken up in EtOAc. The organic phase was washed with 1N aqueous HCl (2×20 ml), 1N aqueous NaOH (2×20 ml) and a saturated aqueous solution of $CuSO_4$. The organic phase was dried ($MgSO_4$) and concentrated to yield Boc—Asp(OBzl)-Lcu-OBzl as a colorless oil. The latter product was treated with 30% TFA in $CH_2Cl_2$ (15 ml). The resulting solution was stirred for 1 h at room temperature. Evaporation of the solvent and residual TFA gave an oily residue which on trituration with Et20-hexane afforded the TFA salt of H—Asp(OBzl)-Leu-OBzl as a white solid.

The preceding coupling procedure was repeated using Boc—Asp(pyrrolidino)—OH (114 mg, 0.4 mmol, described in example 2), the above TFA salt, BOP (177 mg, 0.4 mmol) and NMM (0.22 ml, 2.0 mmol) in acetonitrile (10 ml). Subsequent deprotection of the coupling product, as described above, gave the TFA salt of H—Asp(pyrrolidino)—Asp(OBzl)-Leu-OBzl as a hygroscopic tan colored solid.

Using the same coupling procedure, the latter TFA salt was coupled to 4-(1-ethylpropylamino)-4-oxobutanoic acid (75 mg, 0.4 mmol, described in example 1) with BOP (177 mg, 0.4 mmol) and NMM (0.22 ml, 2.0 mmol) in acetonitrile (10 ml). After work up, the protected product, $Et_2$CHNHCOCH$_2$CH$_2$CO—Asp(pyrrolidino)—Asp(OBzl)-Leu-OBzl, was purified by flash chromatography ($SiO_2$, eluent: EtOAc).

The purified protected product was subject to hydrogenolysis in EtOH (25 ml) for 3 h at atmospheric pressure using 10% by weight of Pd on carbon (100 mg). Thereafter, the catalyst was removed by filtration through diatomaceous earth and the filtrate was evaporated to dryness. The residue was triturated with $Et_2O$ to give the title compound as a white solid (95% pure as indicated by HPLC), MS: 606 $(M+Na)^+$.

EXAMPLE 11

Preparation of
$Et_2$CHNH—COCH$_2$CH[(S)-C(CH$_3$)$_3$]CO—Asp(pyrrolidino)— Asp(cyPn)-γMeLeu—OH (a) A solution of Boc-γMeLeu-OBzl (0.272 g, 0.81 mmol) in 30% TFA in $CH_2Cl_2$ was stirred at 0° for 1 h. The solvent was evaporated and the residue was dried under vacuum. The resulting TFA salt was dissolved in acetonitrile (20 mL). NMM (0.53 mL, 4.86 mmol) was added to the solution, followed by the addition of (S)-α-azido- 1-[(phenylmethoxy)carbonyl]cyclo-pentaneacetic acid (0.269 g, 0.89 mmol, described in example 7) and BOP (0.464 g, 1.05 mmol). The mixture was stirred at room temperature for 18h. The solvent was evaporated. The residue was dissolved in EtOAc (50 mL). The solution was washed with 10% aqueous HCl (2×25 mL), a sainted aqueous solution of $Na_2CO_3$ (2×25 mL) and brine (25 mL). Evaporation of the organic phase gave N-{(S)-α-azido-1-[ (phenylmethoxy)-carbonyl]cyclopentaneacetyl}-2(S)-amino-4,4-dimethylpentanoic acid benzyl ester as a yellow oil (0.400 g, 96% yield).

(b). A solution of the latter compound (0.312g, 0.6 mmol) in MeOH (20 mL) was added dropwise to a solution of $SnCl_2$ (0.207 g, 1.2 mmol) in MeOH (10 mL) at 0°. The mixture was stirred under argon for 4h while the reaction temperature was allowed to come to room temperature. The reaction mixture was concentrated under reduced pressure. The residue was dissolved in EtOAc (50 mL). The solution was rendered basic by the addition of 5% aqueous $NaHCO_3$. The organic phase was separated, washed with $H_2O$ (20 mL) and brine (20 mL), dried over anhydrous $K_2CO_3$, filtered and concentrated to dryness to give N-{(S)-α-amino-1-[ (phenylmethoxy)carbonyl]cyclopentaneacetyl}-2(S)-amino-4,4-dimethylpentanoic acid benzyl ester as a white solid (0.300 g, 0.6 mmol).

(c) The latter amine was dissolved in acetonitrile (20 mL). NMM (0.39 mL, 3.6 mmol), Boc—Asp(pyrrolidino)—OH (0.343g, 1.2 mmol, described in example 2) and BOP (0.583 g, 1.32 mmol) were added to the solution. The mixture was stirred at room temperature for 18 h. The solvent was evaporated and the residue was dissolved in EtOAc (50 mL). The solution was washed with 10% aqueous HCl (2×20 mL), a saturated aqueous solution of $Na_2CO_3$ and brine. Thereafter, the solution was dried ($MgSO_4$) and concentrated to dryness. The residue was purified by flash chromatography [$SiO_2$, eluent=EtOAc-hexane (1:1)]to give N'-[N-(tertiarybutyloxycarbonyl)- 2(S)-amino-4-oxo-4-pyrrolidinobutanoyl]-N-{α-amino- 1-[(phenylmethoxy)carbonyl]cyclopentane-acetyl}-2(S)-amino- 4,4- dimethylpentanoic acid benzyl ester [Boc—Asp(pyrrolidino)—Asp(cyPn)-γMeLeu—OH dibenzoate]as a colorless foam (0.459 g, 100%).

(d) A solution of the latter compound (0.385 g, 0.5 mmol) in 30% TFA in $CH_2Cl_2$ was stirred at 0° for 1 h. The solvent was evaporated and the residue was dried under vacuum. The resulting TFA salt, dissolved in acetonitrile (20 mL), was coupled with (R,S)-2-(1,1-dimethylethyl)- 4-oxo-4-(1-ethyl-propylamino)butanoic acid (0.146 g, 0.6 mmol, described in example 9) using BOP (0.309 g, 0.7 mmol) and NMM (0.65 mL, 6 mmol) according to the procedure described in paragraph (c) of this example. The resulting product was a mixture of two diastereoisomers. The isomers were separated by flash chromatography ($SiO_2$, eluant= EtOAc) to give a less polar isomer [0.100 g, Rf 0.71 (EtOAc)] and a more polar isomer [0.120 g, Rf 0.42 (EtOAc)]. The more polar isomer, namely the di(benzyl ester) of the title compound of this example, was subjected to hydrogenolysis [10% Pd/C in EtOH, 1 atmosphere of $H_2$, 3 h]. After the completion of the reaction, the catalyst was removed from the reaction mixture by filtration through a 45 μM membrane and the filtrate was concentrated. The residue was triturated with $Et_2O$. The resulting white solid was collected and dried under vacuum to give the title peptide of this example (51 mg, 53% yield, 92% pure as determined by HPLC).

In conjunction with the appropriate intermediates, the serial coupling and deprotection procedures of examples 10 and 11 can be used to prepare the compounds of formula 1, such as those exemplified in the table of the following example. In some cases, precipitation of the final product, as described in example 10, does not afford pure material. In those instances, the product was purified by semipreparative HPLC on a C-18 reversed-phase column using 0.06% aqueous TFA-0.06% TFA in acetonitrile gradients. To this end, the crude product was dissolved in 0.1M aqueous $NH_4OH$ and the pH of the solution was brought back to about 7 using 0.1 M aqueous AcOH, prior to purification. When applicable, diastereoisomeric mixtures were separated in this fashion.

Commercially available Boc-amino acids were used. Unnatural amino acids were used in their Boc protected form; they were either commercially available, readily prepared from commercially available corresponding amino acids by reaction with di-tertiary-butyl carbonate, or prepared by standard methods.

Note that N-alkylated Boc amino acids are commercially available or they can be prepared by standard N-alkylation of corresponding Boc-amino acids. For example, Boc—N—Me—Asp(NEt$_2$)—OH was obtained by reacting Boc—Asp(NEt$_2$)—OH with 2.5 molar equivalents of methyl iodide and 2.1 molar equivalents of potassium hydride in THF at 0° for 18 h to give a mixture of Boc—N—Me— Asp(NEt$_2$)—OH and its corresponding methyl ester. The mixture was esterified fully (diazomethane) and then saponified (NaOH/$H_2O$/dioxane) to yield the desired compound.

EXAMPLE 12

Inhibition of Herpes Simplex Virus (HSV, type 1) Ribonucleotide Reductase a) Preparation of Enzyme HSV-1 ribonucleotide reductase (partially purified) was obtained from quiescent BHK-21/C13 cells infected with strain F HSV-1 virus at 10 plaque forming units/cell as described by E. A. Cohen et at., J. Gem Virol., 66, 733 (1985).

b) Assay and Results for Exemplified Peptides

By following the procedure described by P. Gaudreau et at., J. Biol, Chem., 262, 12413 (1987), the assay results listed in the following table were obtained. The assay result for each exemplified compound of formula 1 is expressed as the concentration of the compound producing 50% of the maximal inhibition ($IC_{50}$) of enzyme activity. The number of units of the enzyme preparation used in each assay was constant, based on the specific activity of the enzyme preparation. The results are relative to the activity obtained in control experiments without the test compound and represent the mean of four assays that varied less than 10% with each other.

TABLE

| Compound of Formula 1 | FAB/MS (M + Na)$^+$ | $IC_{50}$ (μM) |
|---|---|---|
| "Title Compound of Example 10" | 606 | 2.9 |
| "Title Compound of Example 11" | 708[3] | 0.17 |
| Et$_2$CHNHCO-(cis-1,2-cyclohexanediyl)-CO-Asp(pyrrolidino)-Asp-Leu-OH | 637 | 3.7 and 2.21 [1] |
| Et$_2$CHNHCO-(cis-CH=CH)-CO-Asp(pyrrolidino)-Asp-Leu-OH | 604 | 21 |
| Et$_2$CHNHCOCH$_2$CH$_2$CO-(N-Me)-Asp(pyrrolidino)-Asp-Leu-OH | 620 | 2.0 |
| Et$_2$CHNHCOCH$_2$CO-Asp(pyrrolidino)-Asp(diMe)-Leu-OH | 634 | 1.4 and 60 [1] |
| Et$_2$CHNHCOCH$_2$CH$_2$CO-Asp(pyrrolidino)-Asp(cyBu)-Leu-OH | 624 [3] | 0.35, 3.6 [1] |
| Cyclohexylamino-COCH$_2$CH$_2$CO-Asp(pyrrolidino)-Asp-Leu-OH | 618 | 22 |
| Et$_2$CHNHCO-(1,2-phenylene)-CO-Asp(pyrrolidino)-Asp-Leu-OH | 654 | 6.5 |
| Me$_2$CHCH$_2$NHCOCH$_2$CO-Asp(pyrrolidino)-Asp-Leu-OH | 592 | 75 [2] |
| Me$_2$CHNHCOCH$_2$CH$_2$CO-Asp(pyrrolidino)-Asp-Leu-OH | 578 | 18 |
| Et$_2$CHNHCOCH$_2$CH$_2$CO-Asp[1(S)-methylheptyloxy]-Asp(cyBu)-Leu-OH | 706 | 4.4 [2] |
| Et$_2$CHNHCOCH$_2$CH$_2$CO-Asp(4-chlorobutyloxy)-Asp-Leu-OH | 643 | 20 |
| Et$_2$CHNHCOCH$_2$CH$_2$CO-NHCH-(2-oxononyl)-CO-Asp-Leu-OH | 635 | 9 |
| Et$_2$CHNHCOCH$_2$CH$_2$CO-NHCH-(2-cyclopentyl-2-oxoethyl)-CO-Asp-Leu-OH | 605 | 3.4 |
| Et$_2$CHNHCOCH$_2$CH$_2$CO-Asp (cyclohexyloxy)-Asp-Leu-OH | 635 | 75 |
| Et$_2$CHNHCOCH$_2$CH$_2$CO-Asp[N(CH$_3$)CH$_2$-CH$_2$OCOCH$_3$]-Asp-Leu-OH | 630 [3] | 9.9 |
| Et$_2$CHNHCOCH$_2$CH$_2$CO-Asp[N(CH$_3$)CH$_2$-CH$_2$OH]-Asp-Leu-OH | 588 [3] | 11 |
| Et$_2$CHNHCOCH$_2$CH$_2$CO-Asp(3,3,5-trimethylhexahydroazepino)-Asp-Leu-OH | 676 | 12 |
| Et$_2$CHNHCOCH$_2$CH$_2$CO-Asp(pyrrolidino)-Asp(diMe)-NH[CH$_2$CH$_2$C(CH$_3$)$_3$] | 604 | 75 |
| Et$_2$CHNHCOCH$_2$CH$_2$CO-Asp(azetidino)-Asp-Leu-OH | 592 | 9.1 |
| Et$_2$CHNHCOCH$_2$CH$_2$CO-Asp(pyrrolidino)-Asp(cyBu)-Leu-OH | 646 | 3.5 |
| Et$_2$CHNHCOCH$_2$CH$_2$CO-Asp (N-Me-N-octyl)-Asp(cyPn)-Leu-OH | 732 | 0.73 |
| Et$_2$CHNHCOCH$_2$CH$_2$CO-Asp(pyrrolidino)-Asp(cyBu)-(L-leucinol) | 632 | 5.0 |
| CH$_3$(CH$_2$)$_2$NHCOCH$_2$CH$_2$CO-Asp (pyrrolidino)-Asp-Leu-OH | 648 | 50 |

[1] Diastereoisomers separable by HPLC
[2] Single diastereoisomer purified by HPLC
[3] (M + H)$^+$ Other examples of the compound of this invention are:
(4F—Ph)CH$_2$CH$_2$NHCOCH$_2$CH$_2$CO—Asp(morpholino)—Asp—Tbg—OH Et$_2$CHNHCOCH$_2$CH$_2$CO—Asp(Net$_2$)-Ψ[CSNH]Asp—Leu—OH MeCH(Cl)CH$_2$NHCOCH$_2$CHEtCO—Asp(Net$_2$)—Asp(diEt)—Leu—OH Et$_2$CHNHCOCH$_2$CH$_2$CO—Asp(pyrrolidino)—Asp(cyPn)— NH[CH$_2$CH$_2$CH(CH$_3$)$_2$]

PhCH$_2$CH$_2$NHCOCH$_2$CHEtCO—Asp(NEt$_2$)Asp(Me)—Cpg—OH

Et$_2$CHNHCOCH$_2$CH$_2$CO—Asp(pyrrolidino)—Asp(Bu)—NH[CH$_2$C(CH$_3$)$_3$]

Et$_2$CHNHCOCH$_2$CH$_2$CO—Asp(pyrrolidino)—Asp(cyPn)-(L-leucinol)

Et$_2$CHNHCOCH](S)—CH(CH$_3$)$_2$]CO—Asp(pyrrolidino)—Asp—Leu—OH

Et$_2$CHNYHCOCH$_2$CH[(S)—C(CH$_3$)$_3$]CO—Asp(pyrrolidino)—Asp(cyPn)— NH[CH$_2$CH$_2$C(CH$_3$)$_3$]

Et$_2$CHNHCOCH$_2$CH](S)—C(CH$_{33}$)]CO—Asp(pyrrolidino)—Asp(cyPn)— (L-γMe-leucinol) and Et$_2$CHNHCOCH$_2$CH[(S)-C(CH$_3$)$_3$]CO—NHCH(3,3-dimethyl-2-oxobutyl)— CO—Asp(cyPn)—γMeLeu—OH)

The embodiments of this invention in which an exclusive property or privilege is claimed are defined as follows:

1. A peptide of formula I

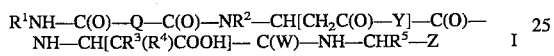

$$R^1NH-C(O)-Q-C(O)-NR^2-CH[CH_2C(O)-Y]-C(O)-NH-CH[CR^3(R^4)COOH]-C(W)-NH-CHR^5-Z \quad I$$

wherein $R^1$ is 1-ethylpropyl, 1-methylethyl or cyclohexyl; $R^2$ is hydrogen or methyl; $R^3$ and $R^4$ each independently is hydrogen, methyl, ethyl or propyl, or $R^3$ and $R^4$ together with the carbon atom to which they are attached form a lower cycloalkyl; $R^5$ is 2-methylpropyl or 2,2-dimethylpropyl; Q is 1,2-ethanediyl, 2,2-dimethyl-1,2-ethanediyl, 2(S)-(1,1-dimethylethy)-1,2-ethanediyl, 2(S)-(1-methylethyl)-1,2-ethanediyl, cis-1,2-cyclohexanediyl, cis-1,2-ethenediyl or 1,2-phenylene; W is oxo; Y is 1-methylheptyloxy, pyrrolidino, 3,3,5-trimethylhexahydroazepino, heptyl, or cyclopentyl; and Z is hydrogen, COOH or CH2OH; the proviso that when Z is hydrogen then $R^3$ is hydrogen, methyl or ethyl and $R^4$ is methyl or ethyl, or $R^3$ and $R^4$ together with the carbon atom to which they are attached form a lower cycloalkyl; or a therapeutically acceptable salt thereof.

2. The peptide as recited in claim 1 selected from the group consisting of:

Et$_2$CHNHCOCH$_2$CH$_2$CO—Asp(pyrrolidino)—Asp—Leu—OH

Et$_2$CHNHCOCH$_2$CH[( S )-C( CH$_3$)3]CO—Asp(pyrrolidino)—Asp(cyPn)-γMeLeu—OH

Et$_2$CHNHCO-(cis-1,2-cyclohexanediyl)—CO—Asp-(Pyrrolidino)—Asp—Leu—OH

Et$_2$CHNHCO-(cis-CH=CH)—CO—Asp(pyrrolidino)—Asp—Leu—OH

Et$_2$CHNHCOCH$_2$CH$_2$CO—(N—Me)—Asp(pyrrolidino)—Asp—Leu—OH

Et$_2$CHNHCOCH$_2$CH$_2$CO—Asp(pyrrolidino)—Asp(diMe)—Leu—OH

Et$_2$CHNHCOCH$_2$CH$_2$CO—Asp(pyrrolidino)—Asp(cyBu)—Leu—OH cyclohexylamino—COCH$_2$CH$_2$CO—Asp(pyrrolidino)—Asp—Leu—OH Et$_2$CHNHCO-(1,2-phenylene)-CO—Asp(pyrrolidino)—Asp—Leu—OH Me$_2$CHCH$_2$NHCOCH$_2$CH$_2$CO—Asp(pyrrolidino)—Asp—Leu—OH Me$_2$CHNHCOCH$_2$CH$_2$CO—Asp(pyrrolidino)—Asp—Leu—OH Et$_2$CHNHCOCH$_2$CH$_2$CO—Asp[1(S)-methylheptyloxy]—Asp(cyBu)—Leu—OH Et$_2$CHNHCOCH$_2$CH$_2$CO—NHCH—(2-cyclopentyl-2-oxoethyl)—CO—Asp—Leu—OH Et$_2$CHNHCOCH$_2$CH$_2$CO—Asp(3,3,5-trimethylhexahydroazepino)—Asp-Leu-OH Et$_2$CHNHCOCH$_2$CH$_2$CO—Asp(pyrrolidino)—Asp(diMe)—NH[CH$_2$CH$_2$C(CH$_3$)$_3$]

Et$_2$CHNHCOCH$_2$CH$_2$CO—Asp(pyrrolidino)—Asp(cyBu)—Leu—OH

Et$_2$CHNHCOCH$_2$CH$_2$CO—Asp(pyrrolidino)—Asp(cyBu)-(L-Leucinol)

CH$_3$(CH$_2$)$_7$NHCOCH$_2$CH$_2$CO—Asp(pyrrolidino)—Asp—Leu—OH

Et$_2$CHNHCOCH$_2$CH[(S)—CH(CH$_3$)$_2$]CO—Asp(pyrrolidino)—Asp—Leu—OH

Et$_2$CHNHCOCH$_2$CH[(S)—C(CH$_3$)$_3$]CO—Asp(pyrrolidino)—Asp(cyPn)-NH[ CH$_2$CH$_2$C(CH$_3$)$_3$] and Et$_2$CHNHCOCH$_2$CH[(S)—C(CH$_3$)$_3$]CO—Asp(pyrrolidino)—Asp(cyPn)-(L-γMe-leucinol).

3. A pharmaceutical composition comprising a peptide as recited in claim 1 or a therapeutically acceptable salt thereof, and a pharmaceutically or veterinarily acceptable carrier.

4. A cosmetic composition comprising a peptide as recited in claim 1 or a therapeutically acceptable salt thereof, and a physiologically acceptable carrier suitable for topical application.

5. A method for treating herpes viral infection in a mammal which comprises administering to the mammmal a peptide as defined in claim 1, or a therapeutically acceptable salt thereof, in an amount effective to inhibit viral ribonucleotide reductase.

6. The method of claim 5 wherein the herpes viral infection is a herpes simplex viral infection.

7. A method of inhibiting the replication of herpes virus which comprises contacting the virus with a herpes viral ribonucleotide reductase inhibiting amount of a peptide as defined in claim 1, or a therapeutically acceptable salt thereof.

8. A method of inhibiting herpes viral ribonucleotide reductase which comprises contacting the ribonucleotide reductase with a peptide as defined in claim 1, or a therapeutically acceptable salt thereof.

* * * * *